United States Patent [19]
Dorsey, III

[11] Patent Number: 5,707,351
[45] Date of Patent: Jan. 13, 1998

[54] REMOTE TUBING ASSEMBLY

[75] Inventor: James H. Dorsey, III, Delray Beach, Fla.

[73] Assignee: C.R. Bard, Inc., Murray Hill, N.J.

[21] Appl. No.: 470,679

[22] Filed: Jun. 6, 1995

[51] Int. Cl.$^6$ ............................................. A61M 1/00
[52] U.S. Cl. ........................... 604/30; 604/35; 604/43
[58] Field of Search ........................... 604/27, 30, 33, 604/35, 43, 48, 264

[56] References Cited

U.S. PATENT DOCUMENTS

| | | | |
|---|---|---|---|
| 4,637,814 | 1/1987 | Leiboff | 604/27 |
| 4,722,725 | 2/1988 | Sawyer et al. | 604/27 |
| 5,100,377 | 3/1992 | Freitas et al. | 604/30 |
| 5,254,083 | 10/1993 | Gentelia et al. | 604/35 |
| 5,360,397 | 11/1994 | Pinchuk | 604/27 |
| 5,496,270 | 3/1996 | Nettekoven | 604/30 |
| 5,542,918 | 8/1996 | Atkinson | 604/27 |

*Primary Examiner*—Corrine M. McDermott
*Attorney, Agent, or Firm*—Darby & Darby

[57] ABSTRACT

A remote tubing assembly is provided which includes a remote tubing attachment which is connected at a first end to a surgical suction/irrigation valve and at a second end to either an instrument insert probe, trocar(s), or a handpiece to provide concurrent smoke evacuation, suction and irrigation at an operative site while a surgeon is simultaneously utilizing surgical hand instruments at the operative site. The remote tubing assembly allows for major smoke removal as well as suction and irrigation while utilizing hand instruments. Thus, the present invention allows a surgeon to concentrate on detailed dissection, while keeping the operative field free of smoke and debris.

23 Claims, 6 Drawing Sheets

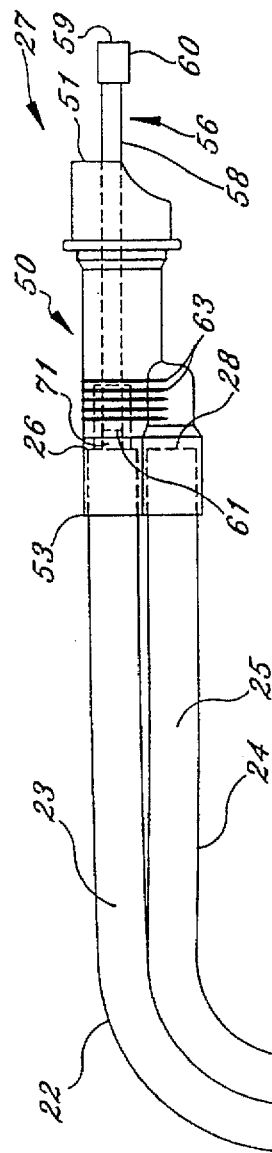
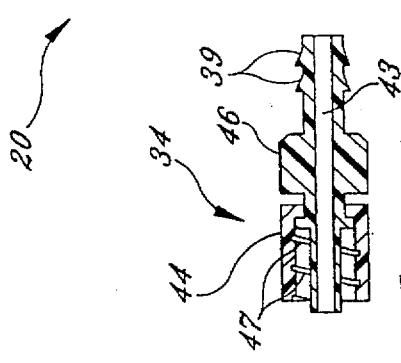
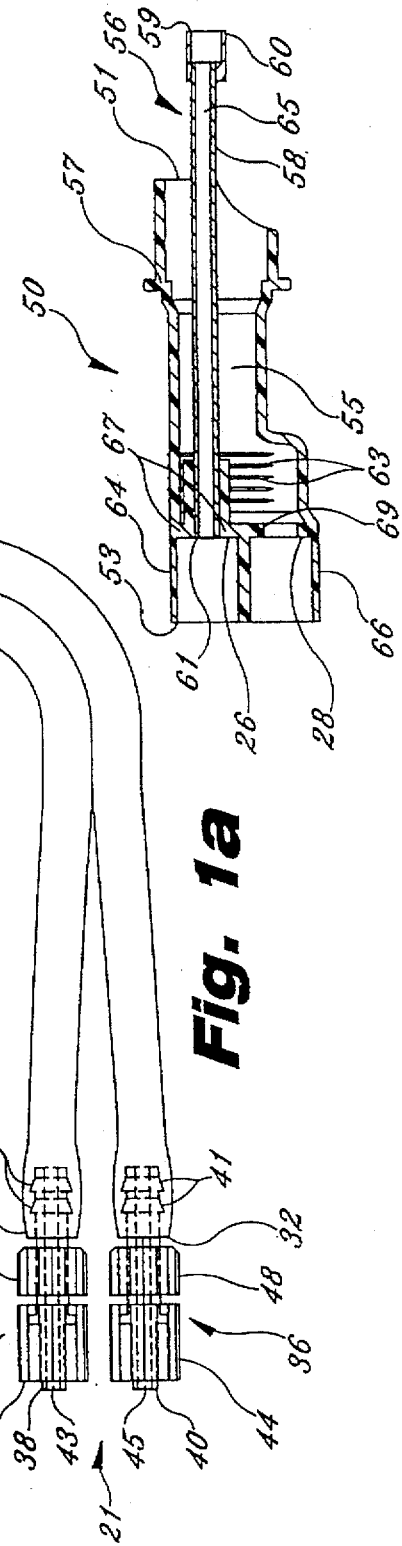
Fig. 1a
Fig. 1b
Fig. 1c

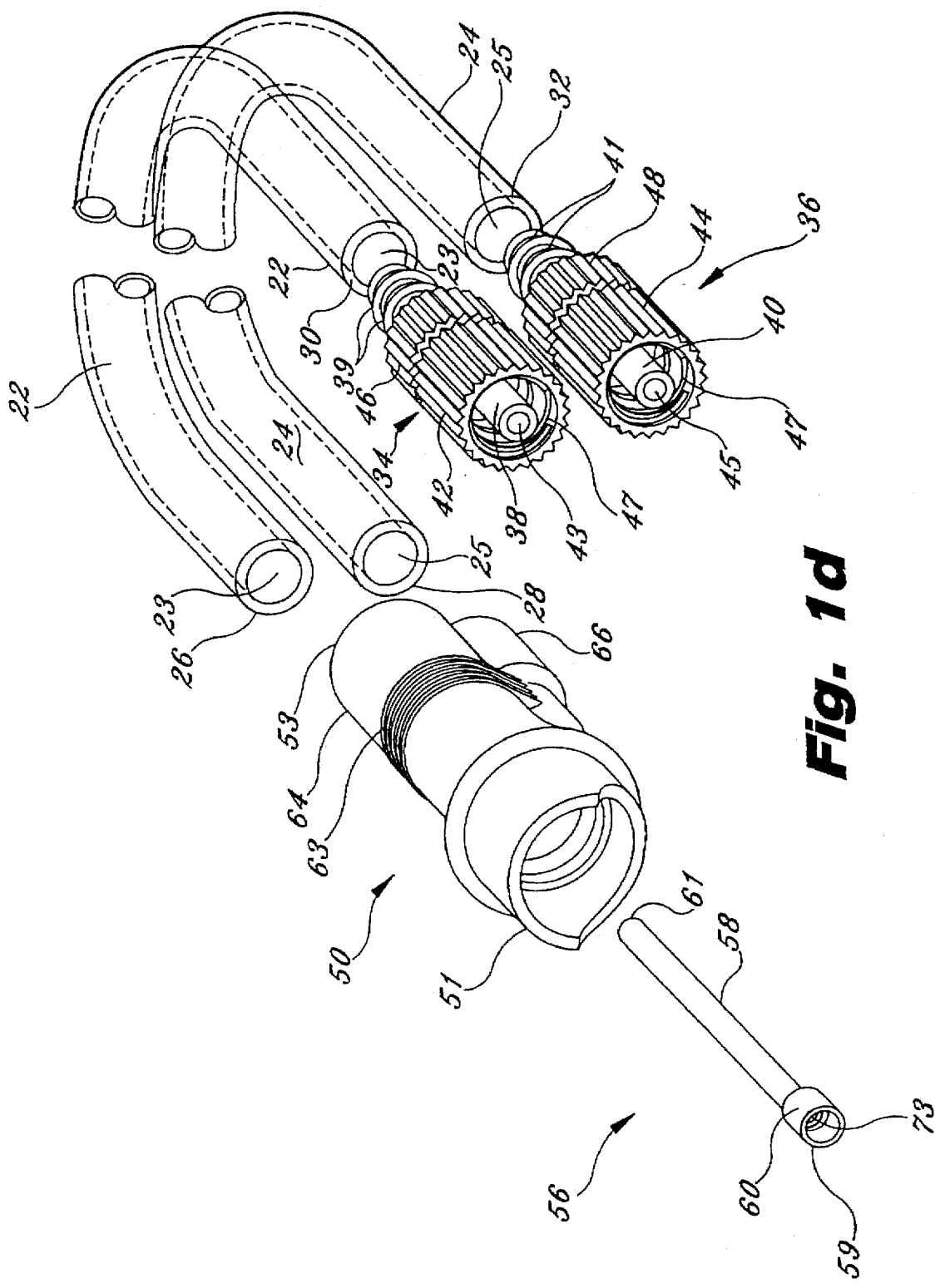

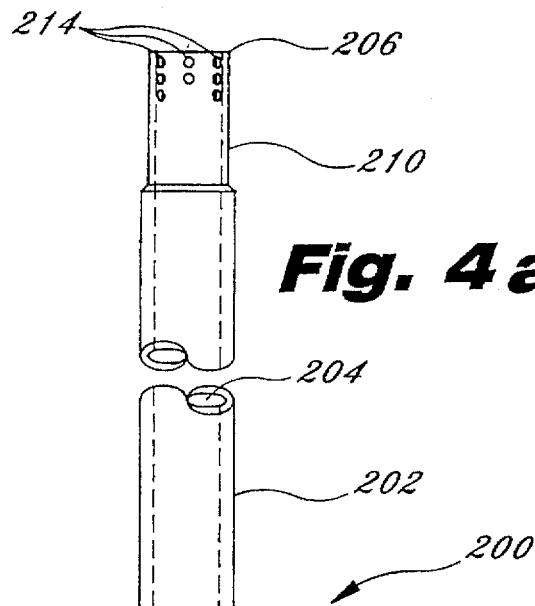
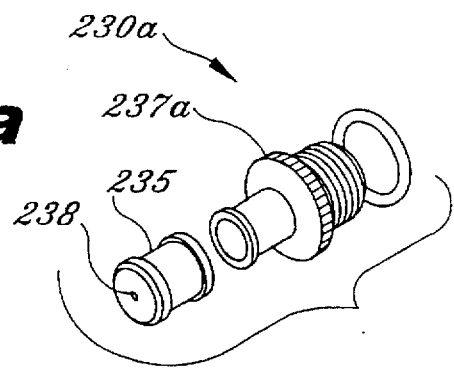
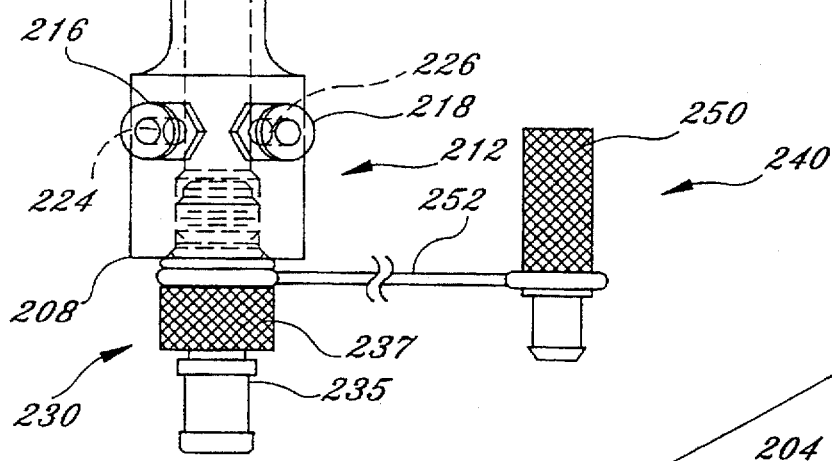
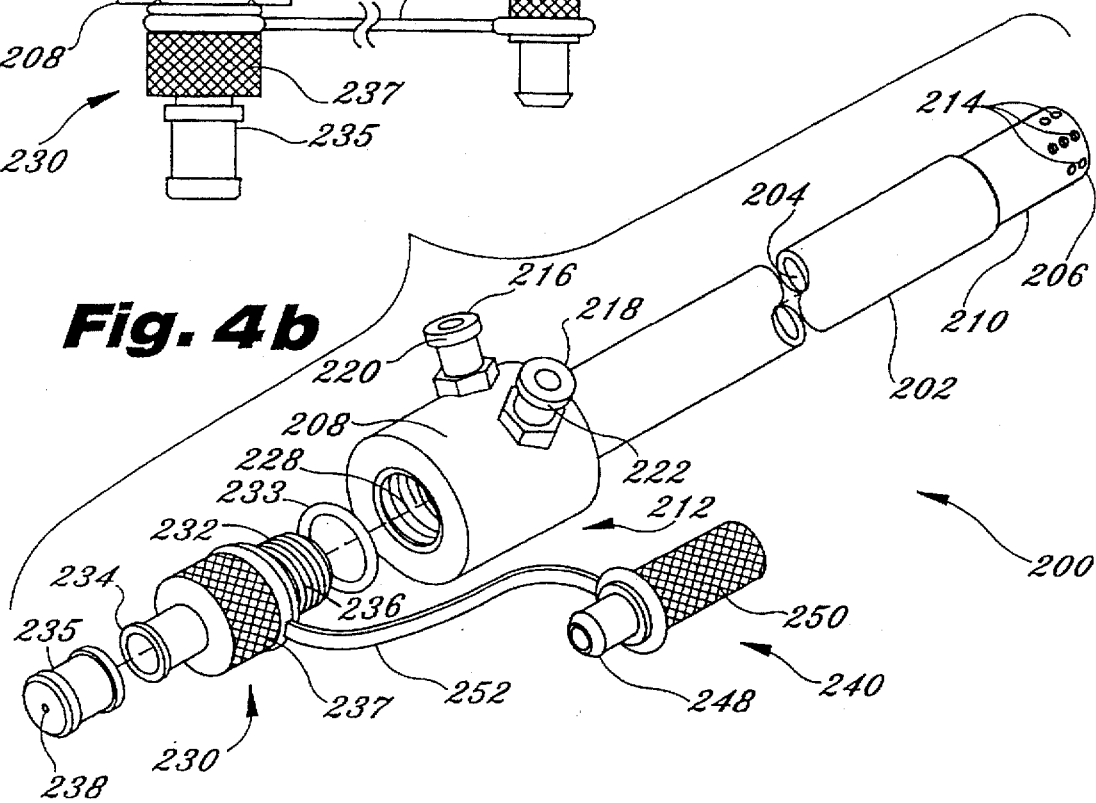
Fig. 4a
Fig. 4c
Fig. 4b

REMOTE TUBING ASSEMBLY

BACKGROUND OF THE INVENTION

1. Field of the Invention

The present invention relates generally to the field of laparoscopic and endoscopic surgery and in more particularly to a specially designed remote tubing attachment assembly which simultaneously allows for concurrent smoke evacuation, suction and/or irrigation in conjunction with a hand-held valve, while a surgeon is utilizing other hand instruments.

2. Description of the Prior Art

During laparoscopic surgery, a form of endoscopic surgery dealing specifically with the abdominal area, a surgeon typically makes several small, spaced incisions through the abdominal wall on an anesthetized patient. A source of compressed CO2 is then provided through one of the incisions to inflate the abdomen, thus raising the abdominal wall above the organs and intestines of the patient. A space is thereby created between the abdominal wall and organs/intestines which allows manipulation of surgical instruments, in conjunction with trocars which have been inserted into the abdomen through at least one of the other incisions.

During laparoscopic surgery, smoke, blood and other debris are generated which can impair the surgeon's vision of the operative site. Accordingly, the smoke, blood and debris must be removed to provide visibility to the surgeon of the operative site. Presently, the surgeon withdraws the surgical instrument he or she was using from the trocar, and inserts through the trocar a suction/irrigation surgical probe attached to a suction/irrigation valve for the removal of the smoke, blood and debris. It is readily apparent that substantial time is utilized removing the smoke, blood and debris. This problem is further magnified when the surgical procedure produces a relatively large amount of smoke, requiring the surgeon to expand a vast amount of time switching probes to remove the generated smoke.

Thus, what is needed in the art, is an attachment assembly which allows a surgeon to utilize hand instruments such as shears and graspers, while at the same time simultaneously providing concurrent smoke evacuation, suction and/or irrigation to the operative site. It is, therefore, to the effective resolution of the aforementioned problems and shortcomings that the present invention is directed.

SUMMARY OF THE INVENTION

The present invention discloses a remote tubing assembly including a remote tubing attachment which is removably connected at a first end to a surgical suction/irrigation valve and at a second end to either an instrument insert probe, trocar(s), or a handpiece to provide concurrent smoke evacuation, suction and irrigation at an operative site while a surgeon is simultaneously utilizing surgical hand instruments at the operative site. The assembly thereby allows for increased visibility at the operative site by allowing for smoke removal, as well as suction and irrigation while utilizing hand instruments through one trocar port. Thus, the present invention allows a surgeon to concentrate on detailed dissection, while keeping the operative field free of smoke and debris.

The remote tubing consists of two isolated flexible tubing members preferably attached to each other along a majority of their respective external surface lengths. The first tubing member provides a smoke evacuation and suction channel which is associated with the suction chamber of the surgical valve. The second tubing member provides an irrigation channel which is associated with the irrigation of the surgical valve. Each tubing member is provided with a barbed swivel luer for removable connection to luer attachments associated with the instrument insert probe, hand piece, and the trocar(s).

One end of the remote tubing attachment separates the common channel of the surgical valve into separate designated suction and irrigation areas. One function of the remote tubing attachment allows a physician who has inserted a 5 mm instrument down through a 5 mm or 10 mm port (trocar) to utilize the normally wasted space in the trocar for controlled smoke evacuation, suction and/or irrigation. The remote tubing can also be connected directly to another object of this invention called an instrument insert probe, thus allowing the smoke evacuation, suction and/or irrigation to be closer to the operative site. This invention allows smoke to be evacuated at the point of origin, thus satisfying ANSI standards.

When utilizing an electrosurgical hand held instrument through the instrument insert probe having the remote tubing attached, smoke is evacuated down as close to the tip of the instrument as possible. This allows for the removal of smoke where it is the densest. Furthermore, if bleeding occurs, a physician can ask a scrub nurse who is holding the trumpet valve to which the other end of the remote tubing is attached to, for irrigation and the irrigation will squirt down alongside the shaft of the instrument insert probe to its desired destination. For suction, the electrosurgical instrument is manually retracted inside the instrument insert probe to allow for pinpoint suction at the desired area.

The remote tubing can be attached directly to the trocar to achieve these same advantages. However, the efficiency of the suction and irrigation functions are increased by the attaching the remote tubing directly to the instrument insert probe. Furthermore, although the remote tubing assembly can be used in conjunction with a trocar, hand piece, or the instrument insert probe, such is not limiting. Conversely to one trocar, each of the two luer locks at the end of the tubing members can be hooked up or connected to an individual trocars or to other suction/irrigation cannulas. When hooked up to two trocars, a first of the two trocars provides suction and the evacuation of smoke and CO2, and the second of the two trocars provides irrigation. Furthermore, to provide suction and irrigation function to a single trocar, a y-connector is provided to interface remote tubing members with the trocar and to provide communication therebetween.

Accordingly, it is an object of the present invention to provide at an operative site concurrent suction/irrigation functions from a remote source through a surgical instrument while a surgeon is utilizing the surgical instrument for other surgical functions.

It is a further object of the present invention to allow for major smoke removal as well as suction and irrigation while utilizing hand instruments.

It is another object of the present invention to increase a surgeon's visibility at an operative site during surgical procedures at the operative site.

It is yet another object of the present invention to reduce the amount of time for removing smoke, blood and debris at an operative site.

It is still another object of the present invention to reduce the amount of surgical time required for various laparoscopic surgical procedures.

It is even still another object of the present invention to allow a surgeon to concentrate on detailed dissection, while keeping the operative field free of smoke, blood and debris.

In accordance with these and other objects which will become apparent hereinafter, the instant invention will now be described with particular reference to the accompanying drawings.

BRIEF DESCRIPTION OF THE DRAWINGS

The invention may be better understood by reference to the drawings in which:

FIG. 1a is a side view of the remote tubing attachment of the present invention;

FIG. 1b is a sectional view of the valve connection member of the remote tubing attachment of FIG. 1a;

FIG. 1c is a sectional view of a luer of the remote tubing attachment of FIG. 1a;

FIG. 1d is an exploded perspective view of the remote tubing attachment of FIG. 1a;

FIG. 2b is a side sectional view of the trocar of FIG. 2a;

FIG. 2c is a perspective view of the valve member of the trocar shown in FIG. 2a in a closed position;

FIG. 2d is a perspective view of the valve member of the trocar shown in FIG. 2a in an open position;

FIG. 4a is a top view of the remote instrument insert of the present invention;

FIG. 4b is a perspective view of the remote instrument insert shown in FIG. 4a;

FIG. 4c is a perspective view of an alternative embodiment for the adaptor of the remote instrument insert;

DESCRIPTION OF THE PREFERRED EMBODIMENTS

Figure 2A:
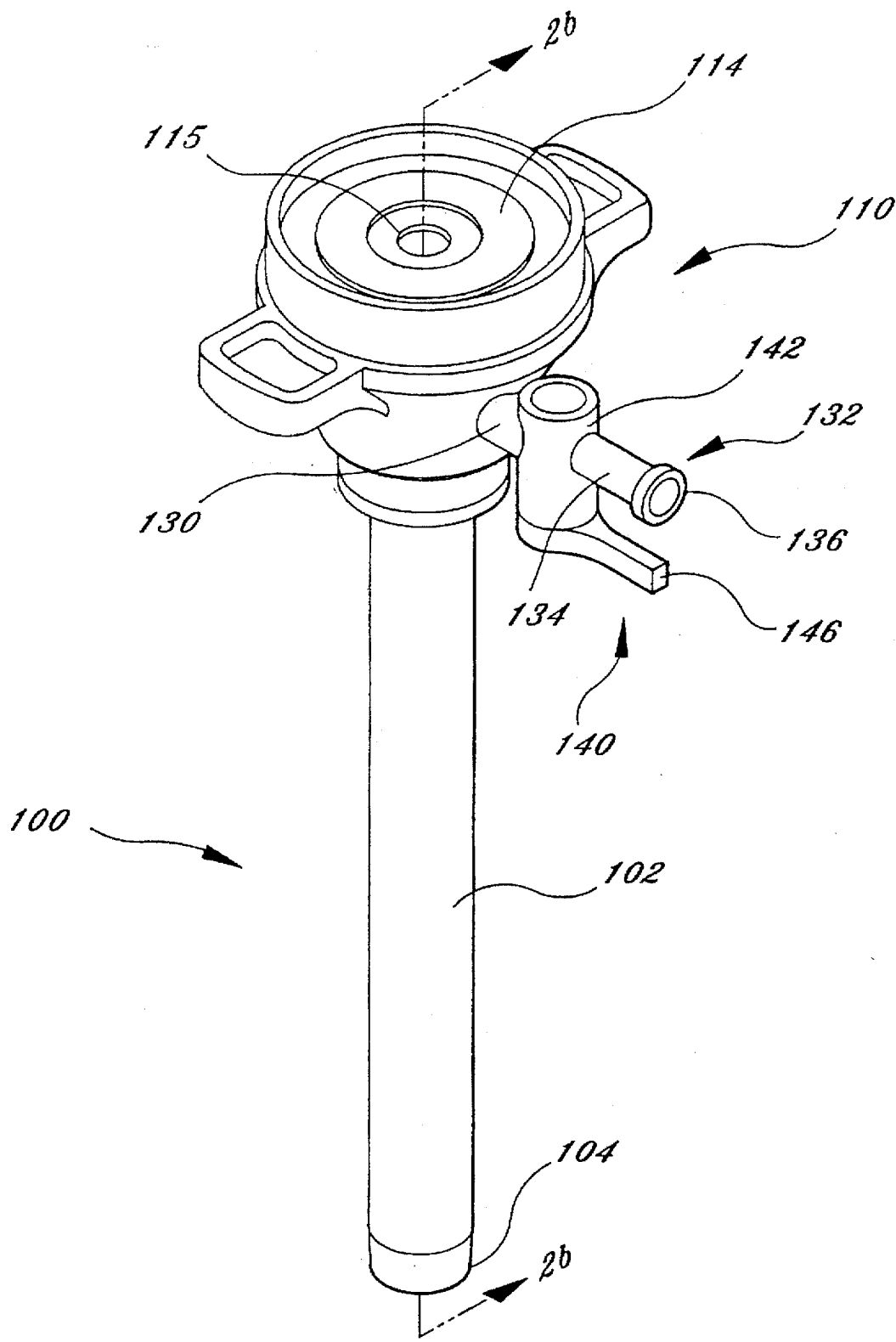
FIG. 2a is a perspective view of a trocar of the present invention.

FIGS. 1a–1c illustrate the remote tubing attachment generally designated as reference numeral 20. Attachment 20 consist of a first elongated flexible tubing member 22 and a second elongated flexible tubing member 24. First tubing member 22 has a first end 26 and a second end 30, while second tubing member 24 has a first end 28 and a second end 32. A first channel 23 is defined between first end 26 and second end 30 of tubing member 22. Likewise, a second channel 25 is defined between first end 28 and second end 32 of tubing member 24. The purpose of channels 23 and 25 will described below. Tubing members 22 and 24 are attached to each other by conventional means along a substantial external surface portion of their respective lengths.

Second ends 30 and 32 of tubing members 22 and 24, respectively, are each provided with a barbed swivel luer 34 and 36, respectively. Luer 34 consists of a rod 38 having a first end and a second end. The first end of rod 38 is operatively associated with a connecting cap 42 by conventional means. The diameter of cap 42 is larger than the diameter of rod 38 to allow the insertion of a mating luer disposed on either a handpiece, remote instrument insert probe, or trocar for the connection of tubing member 22 to such surgical instrument. Accordingly, cap 42 functions as a female receiving means for the connection of tubing member 22 with the above-identified surgical instruments. This connection will be fully discussed below. The inside surface of cap 42 is provided with either threads or ramps 47 for mating with either threads or ramps on the luer of the surgical instrument. Cap 42 is connected to rod 38 in such manner to permit cap 42 to spin around rod 38.

Rod 38 is also provided with a stationary cap 46 disposed along rod 38 intermediate cap 42 and the second end of rod 38. The diameter of stationary cap 46 is larger than the diameter of rod 38 to allow the insertion of an end 30 of tubing member 22 when luer 34 is attached to tubing member 22. Accordingly, cap 46 functions as a female receiving means for the connection of tubing member 22 with luer 34. The diameter of rod 38 can be larger at the second end of rod 38 as compared to the diameter at the first end. This causes tubing member 22 to slightly expand, thus, providing a snug and tight fit which provides a sealed connection when end 30 of tubing member 22 is received by cap 46, thus attaching tubing member 22 to luer 34. The second end of rod 38 can also be provided with one or more protrusions 39 to further ensure the sealed connection between tubing member 22 and luer 34.

Luer 36 is constructed and connected to end 32 of tubing member 24 similar to the construction and connection of luer 34 to end 30 of tubing member 22. As such, luer 36 is provided with rod 40, connecting cap 44 and stationary cap 48. Similar to rod 38, rod 40 can be provided with one or more protrusions 41 to further ensure a sealed connection between tubing member 24 and luer 36. Also similar to rod 38, the diameter at the second end of rod 40 may be larger than the diameter at the first end. A drop or two of adhesive (not shown) can be can be provided where ends 30 and 32 are inserted within caps 46 and 48, respectively, to further ensure luers 34 and 36 remain attached to tubing members 22 and 24, respectively.

Rod 38 defines an elongated channel 43 extending from its first end to its second end. Thus, when luer 34 is connected to tubing member 22, channel 43 is in communication with channel 23 of tubing member 22. Likewise, rod 40 defines an elongated channel 45 extending from its first end to its second end. Accordingly, when luer 36 is connected to tubing member 24, channel 45 is in communication with channel 25 of tubing member 24. Luers 34 and 36, and their corresponding components, as well as their attachments to ends 30 and 32, of tubing members 22 and 24, respectively, will generally be referred to as the first end 21 of the remote tubing attachment 20.

Second end 27 of remote tubing attachment 20 generally consists of first ends 26 and 28 of tubing members 22 and 24, respectively, and a valve connection member generally designated as reference numeral 50. Valve connection member 50 has a first end 51 and a second end 53. Second end 53 defines tube insertion ports 64 and 66. The inside diameters of ports 64 and 66 are slightly larger than the diameters of tubing members 22 and 24. Thus, to connect the tubing members 22 and 24 to valve connection member 50, end 26 of tubing member 22 is inserted within port 64 and end 28 of tubing member 24 is inserted within port 66. Prior to insertion a drop or two of adhesive (not shown) may be provided on ends 26 and 28 to help maintain a strong connection between tubing members 22 and 24 and valve connection member 50.

Ports 64 and 66 are isolated from each other. However, ports 64 and 66 terminate ultimately into a common channel 55 within valve connection member 50. Ports 64 and 66 are each provided with a back wall 67 and 69, respectively, to prevent ends 26 and 28 of tubing members 22 and 24, respectively, from being inserted into common channel 55. Back wall 67 is further provided with a recess 71 for purposes discussed below.

End 51 of valve connection member 50 is attached to a valve, such as a hand held trumpet valve 80. The valve may have the quick disconnect attachment feature as disclosed in co-pending invention U.S. application Ser. No. 08/286,949, which is incorporated by reference herein. End 51 is received by one of the probe mounts 82 of valve 80, until end 51 is abutting the outer wall of the associated valve chamber 84 of valve 80. The inner diameter of connection member 50 may be reduced at point 57, to provide a snap-lock fit with an o-ring 85 of removable adaptor 96 which is attached to probe mount 82, when end 51 is fully received by probe mount 82. In another embodiment, the adaptor 86 may be constructed integrally with probe mount 82. In either embodiment, the removable connection of end 51 to probe mount 82 is the same. Additionally, a cap 97 having a body member 95 may be provided at the other probe mount of valve 80. An o-ring may be associated with cap 97 for sealing purposes.

One or more protrusions, providing a tactile gripping surface 63, may be disposed on the outer surface of a portion of valve connection member 50 to aid in the attachment and disattachment of end 51 to valve 80.

Valve 80 is provided with a common channel 88, which communicates with the irrigation chamber 84a and the suction chamber 84b of valve 80. When the valve is in use, to provide simultaneous suction and irrigation, common channel 88 must be separated in such a way to isolate the suction from the irrigation. Furthermore, in addition to isolating common channel 88 of valve 80, common channel 55 of valve connection member 50 must also be separate to ensure that irrigation is directed to its dedicated port 64 and that suction and smoke evacuation enters common channel 55 without interfering with the flow of irrigation, as well as contaminating the irrigation.

Accordingly, a separation means generally designated 56 is attached to said valve connection member 50 and disposed substantially within common channel 55 of connection member 50. Separation means 56 consist of an elongated hollow rod 58 which defines an irrigation channel 73 extending from a first end 59 of rod 58 to a second end 61 of rod 58. The diameter of rod 58 is greater at first end 59 as compared to the remaining portion of rod 58 to define a first boss member 60 at the first end 59 of rod 58.

To attach rod 58, second end 61 is inserted within recess 71 of back wall 67 to provide communication between tubing member 22 and irrigation channel 65. A drop of adhesive (not shown) may be provided at second end 61 of rod 58 to ensure a strong connection. Once rod 58 is properly attached, smoke, blood and other debris, which has been suctioned or removed from the operative site, is prevented from entering tubing member 22 and interfering with the flow of irrigation, as well returning to the surgical area from which they were previously removed. Additionally, once rod 58 is attached, end 61 and a substantial length of the middle portion of rod 58 are disposed within channel 55. Thus, first end 59 and the remaining length of the middle portion of rod 58 are protruding outward from valve connection member 50.

When connection valve member 50 is attached to either one of the probe mounts 82 of valve 80, end 59 is disposed within common channel 88 intermediate the two openings 86 communicating common channel 88 with valve chambers 84. The inner diameter of common channel 88 is slightly larger than the outside diameter of boss 60 to accommodate boss 60 and end 59 within channel 88, while at the same time effectively separating channel 88 into a suction area 90 and an irrigation area 92 which are isolated from each other. Accordingly, the portion of common channel 88 in communication with irrigation channel 65 will also be operatively associated with the irrigation chamber 84a.

To supply a source of irrigation to one of the above-identified surgical instruments, a user, such as a scrub nurse, simply depresses the irrigation valve 94a causing a source of irrigation to travel from the irrigation chamber 84a to the designated portion of common channel 88 through irrigation channel 65 of rod 58 into port 64 and tubing member 22. The source of irrigation will then travel through tubing member 22 to the surgical instrument which is being held by the physician or surgeon. Likewise, where debris or blood is required to be removed, the scrub nurse depresses the suction valve 94b causing the debris to travel through the surgical instrument held by the physician through tubing member 24 through port 66 through common channel 55 of tubing connector 50 to the designated portion of common channel 88 of valve 80 and ultimately through the suction chamber 84b of valve 80.

As ports 64 and 66 are isolated from each other and common channel 88 is divided into separate designated suction and irrigation areas 90 and 92, respectively, by boss members 60, simultaneous suction and irrigation can be provided by valve 80 at an operative site (not shown). In lieu of suction, the valve can be set by a metering means 98 for continuous smoke evacuation or removal at an operative site, while simultaneously providing for a source of irrigation at such operative site. The subject matter is disclosed in co-pending invention U.S. application Ser. No. 08/139,948, which is incorporated by reference herein.

Whether luers 34 and 36 of the remote tubing attachment 20 are being attached to a trocar(s), remote instrument insert probe, handpiece or a y-connector associated with a trocar, end 27 of tubing attachment 20 always is associated with a valve, such as trumpet valve 80, described above. Accordingly, valve 80 can remain attached to end 27 while the tubing attachment is interchangeably used between the trocars, remote instrument insert probe, handpiece and y-connector.

Figures 2B, 2C, 2D:
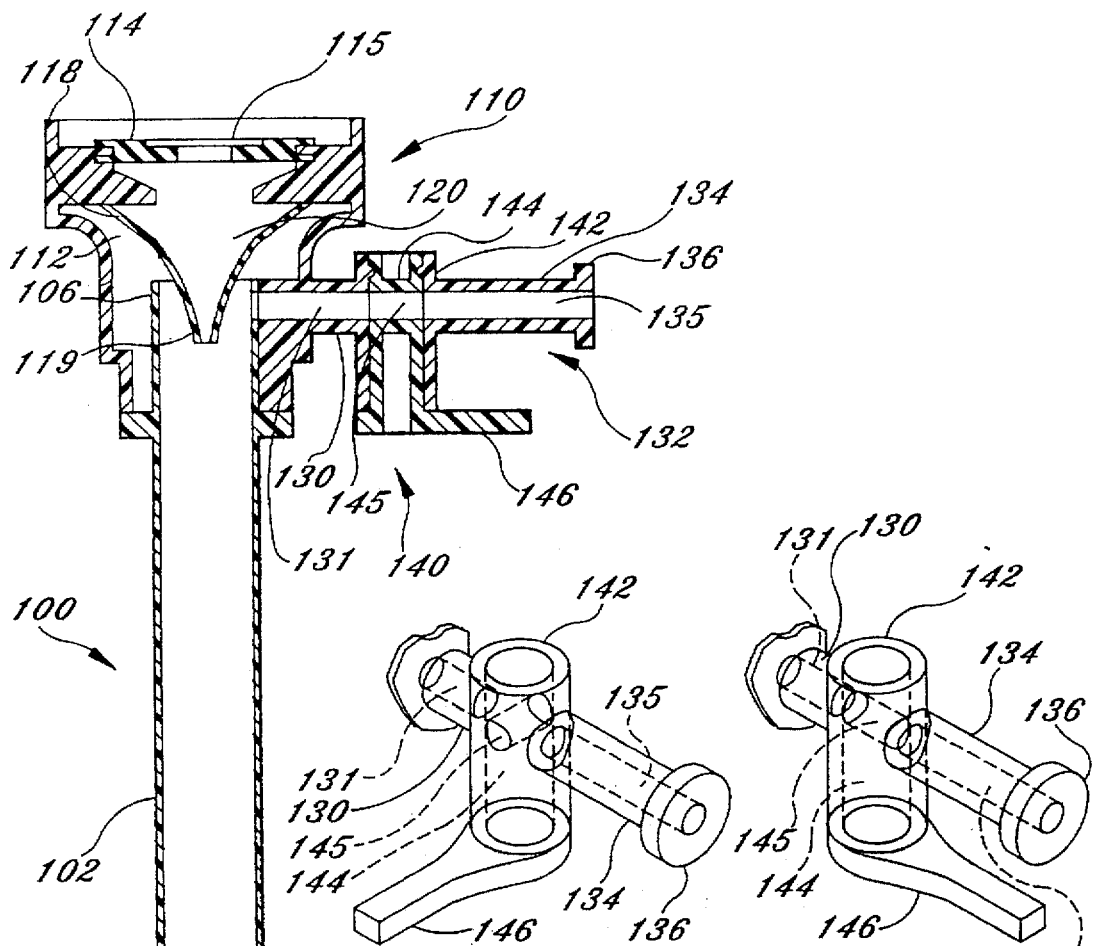
Figure 3:
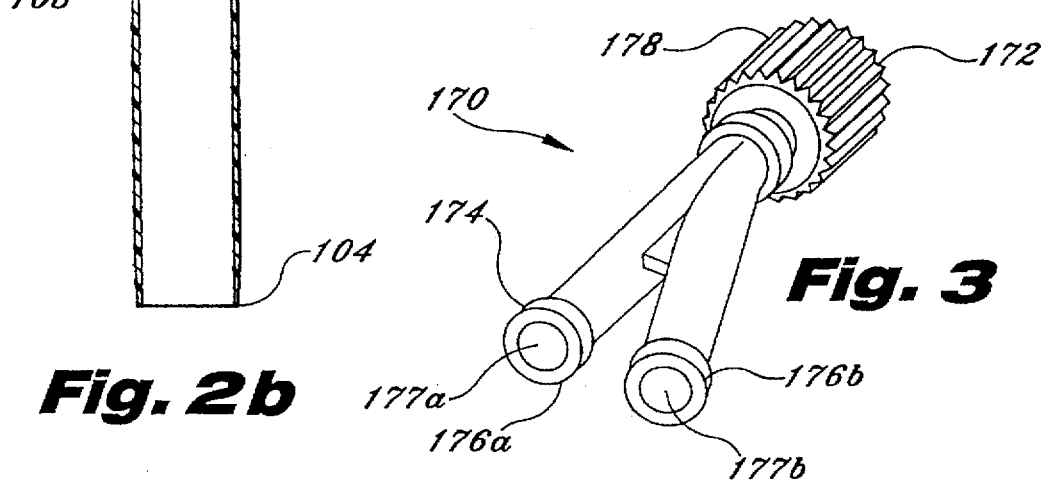
FIG. 3 is a perspective view of a y-connector of the present invention.
Figure 5:
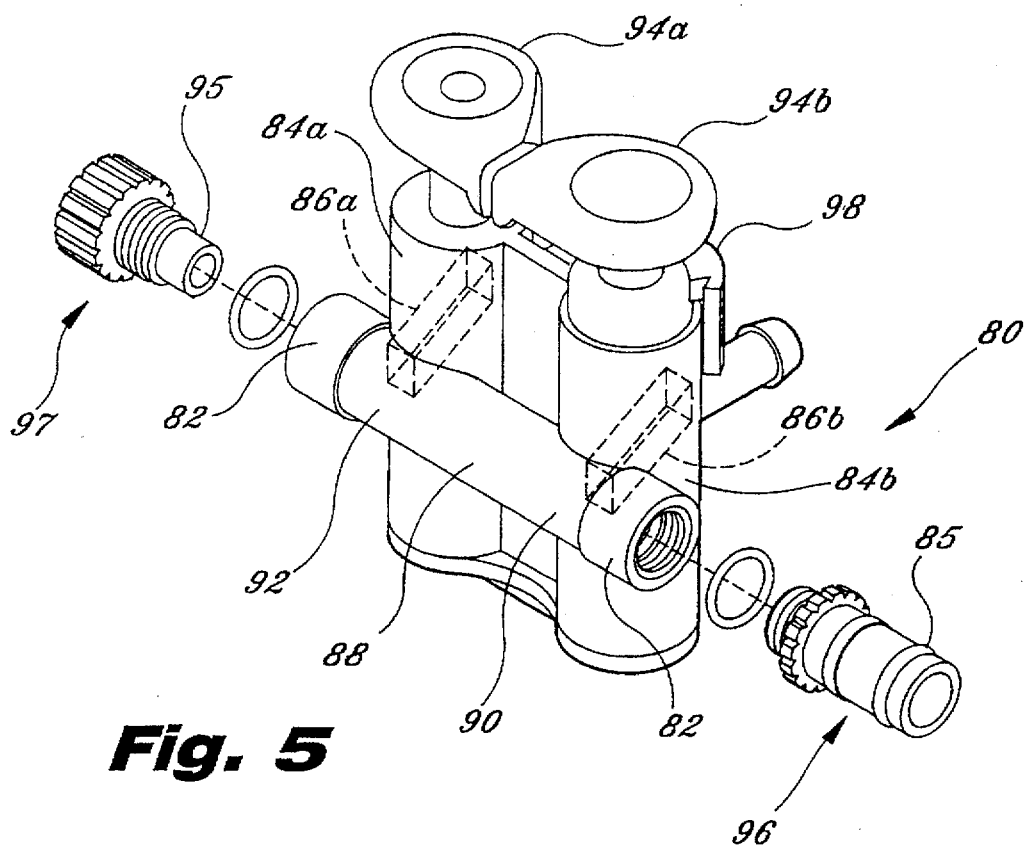
FIG. 5 is a perspective view of a trumpet valve which is used with the present invention.
Figure 6:
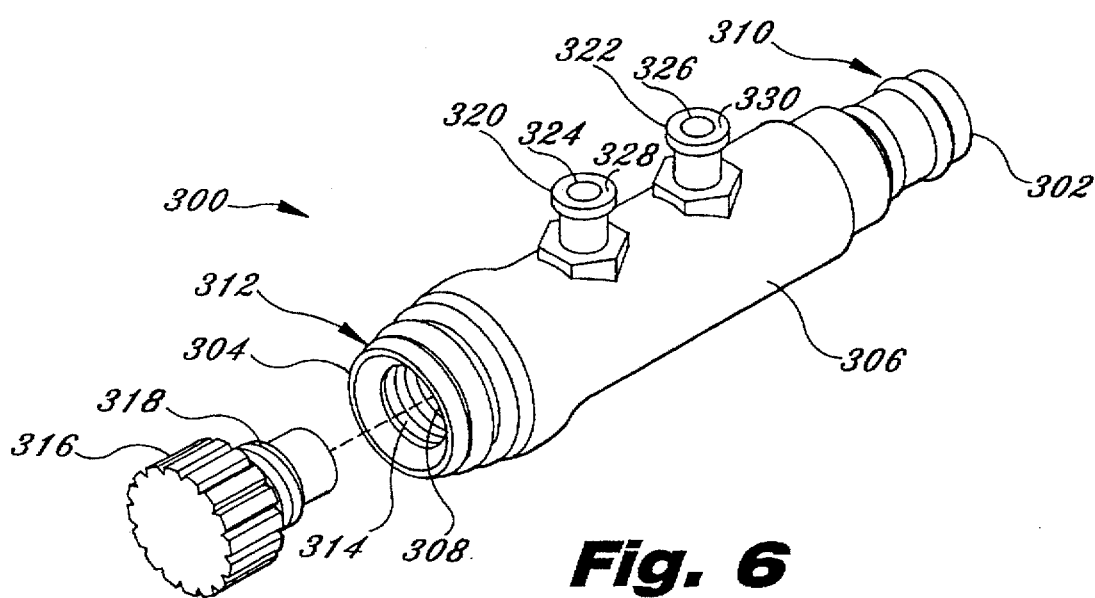
FIG. 6 is a perspective view of a handpiece of the present invention.

FIGS. 2a–2d illustrate a trocar 100 which can be connected directly to the remote tubing attachment 20 to provide suction and irrigation at the operative site. Trocar 100 generally consist of an elongated hollow shaft 102 having a first end 104 and a second end 106, the second end being attached to a receiving base 110. A passageway 108 is defined by shaft 102 extending from first end 104 to second end 106. The elongated shaft 102 of trocar 100 is inserted into the abdomen through an incision, thus creating a large opening through shaft 102 to allow access into the abdomen area for the manipulation of surgical instruments.

Receiving base 110 defines a passageway 112 which is in communication with passageway 108 defined by shaft 102. A flexible plug member 114 having an opening 115 is disposed near the top surface of base 110. A flexible valve member 118 is disposed within passageway 112. Valve 118 is substantially conically shaped, thus, forming an open tip end 119 which is received within passageway 108 at the second end 106 of shaft 102. Valve member 118 and plug member 114 provide a friction fit when surgical instruments are inserted through passageway 102 for use at the operative site.

Trocar 100 is also provided with a side conduit 130, defining a passageway 131, which is in communication with passageway 108 of elongated shaft 102. Attached to side conduit 130 is a luer connector 132. Preferably, luer connector 132 is formed integral with side conduit 130. Luer connector 132 generally consists of a conduit 134 having a luer attachment member 136 disposed at its distal end, and a shutoff valve member 140. Conduit 134 defines a passageway 135 extending from its proximal end to its distal end. Conduit 134 and luer attachment member 136 act as a male insertion member for either female receiving luer 34 or 36 of remote tubing attachment 20. Luer attachment member 136 can be either a thread or a ramp portion disposed at the distal insertion end conduit 134 for mating with either luer 34 or 36.

Valve member 140 controls communication between passageway 131 of side conduit 130 and passageway 135 of conduit 134. Valve member 140 generally consists of a cylinder 142, blocking member 144 is disposed within cylinder 142, and a handle member 146 operatively associated with blocking member 144. Blocking member 144 defines a passageway 145 extending from the first end to the second end of blocking member 144, which can be aligned with passageways 131 and 135 for communication by turning handle 146.

Turning handle 146 positions the side surface area of blocking member 144 in the direct path of communication, thus, effectively cutting off communication between passageways 131 and 135, or aligns passageway 145 with passageways 131 and 135 to provide communication between passageways 131, 145 and 135 and ultimately providing communication between an attached tubing member 22 or 24 with passageway 108 of trocar 100.

If either suction/smoke evacuation or irrigation desired at the operative site associated with trocar 100, the respective tubing member 22 or 24 is connected, via its respective luer, to luer connector 132 by mating luer 34 or 36, respectively, to luer attachment 136. For example, in this situation, tubing member 22 can be connected to a first trocar to provide irrigation at the associated operative site, while tubing member 24 can be similarly connected to a second trocar to provide suction/smoke evacuation at a different operative site. Thus, valve 80 can simultaneously service two different operative sites.

To provide both suction/smoke evacuation and irrigation to the same operative site, in conjunction with trocar 100, a y-connecter 170 is provided between trocar 100 and tubing members 22 and 24. Y-connector 170 consist of a trocar attachment end 172 and a tubing attachment end 174. Tubing attachment end 174 consist of two male insertion members 176a and 176b, each resembling conduit 134 and luer attachment 136. A cap 178 is disposed at trocar attachment end 172 and functions similar to, as well as being structurally similar to, caps 42 and 44 disposed at the respective ends of tubing members 22 and 24. Male insertion members 176a and 176b define passageways 177a and 177b, respectively, which converge into a single passageway (not shown) defined by trocar attachment end 172.

Cap 178 receives luer attachment 136 of luer connector 132, to connect end 172 of y-connector 170 to trocar 100. Once connected, the single passageway defined by trocar attachment end 172 and passageways 177a and 177b are in communication with passageways 131, 135 and 145, and ultimately passageway 108 of elongated shaft 102 when blocking member 144 is in its communication position. Luers 34 and 36, respectively receive male insertion members 176a and 176b, to connect end 174 of y-connector 170 to tubing members 22 and 24, respectively. Once the tubing members have been connected communication between valve 80 and trocar 100 is completed thus allowing for both suction/smoke evacuation and irrigation at trocar 100. Smoke and debris removed from the operative site will travel through one of the passageways 177 of insertion members 176 of y-connector 170 and ultimately to valve 80, while irrigation will travel through the other insertion member from valve 80 to the operative site (not shown).

In addition to attaching tubing members 22 and 24 to trocar 100, either directly or indirectly through y-connector, tubing members 22 may be attached to a remote instrument insert probe generally designated as reference numeral 200. Insert probe 200 has a first end 206 and a second end 208, as well as an elongated shaft 202. Elongated shaft 202 defines a passageway 204 extending from first end 206 to second end 208. A tip member 210 is disposed at first end 206. A plurality of apertures 214 are provided along tip member 210 for suctioning debris and blood, as well as for smoke evacuation.

A base member 212 is disposed at the second end 208 of insert probe 200. A pair of luer attachments 216 and 218 protrude outward from base member 212. Luer attachments 216 and 218 define internal passageways 224 and 226, respectively, which are in communication with passageway 204. Luer attachments 216 and 218 act as male insertion members for mating with female receiving luers 34 and 36 and have either mating threads or mating ramp portions 220 and 222, respectively, disposed at their distal insertion ends.

Caps 42 and 44 of luers 34 and 36, respectively, receive luer attachments 216 and 218, to connect respective tubing members 22 and 24 to remote instrument insert probe 200. Once connected, passageways 23 and 25 are in communication with respective passageways 224 and 226 and, thus, in communication with passageway 204 of insert probe 200. Once the tubing members have been connected communication between valve 80 and insert probe 200 is completed thus allowing for both suction/smoke evacuation and irrigation at the operative site through insert probe 200. Smoke and debris removed from the operative site will travel through the opening at first end 206 and the apertures 214 of tip member 210 and through passageway 204 of elongated shaft 202 to the associated suction/smoke evacuation luer attachment 216 or 218 and ultimately to valve 80, while irrigation will travel from valve 80 through the other luer attachment through passageway 204 to the operative site. To connect luer attachments 216 and 218 to base member 212, luer attachments 216 and 218 can be disposed in or threaded with corresponding apertures in the side of base member and retained by adhesive.

At least a portion of passageway 204 which is defined by base member 212 is provided with threads 228 for mating with threads 236 of a first end 232 of adaptor member 230. An o-ring 233 may be disposed on adaptor 230 for sealing purposes. A flexible hood 235 is disposed over the second end 234 of adaptor member 230. Hood 235 is provided with an aperture 238 for insertion of various relatively narrow surgical instruments inserts such as electrodes, etc. (not shown) and provides a friction fit when such instruments are inserted through aperture 238. Hood 235 may be removed to expose the second end 234 of adaptor 230. Second end 234 is open for insertion of larger surgical instruments such as shears, graspers, etc. (not shown) which would not fit through aperture 238. Adaptor 230 may be provided with a knurled surface 237 to aid in attaching adaptor 230 to base member 212 of remote instrument insert 200.

An alternative adaptor is generally shown as reference numeral 230a. Adaptor 230a is similar to adaptor 230 except for a small handling surface 237a in lieu of the knurled surface area 237 of adaptor 230.

A lanyard 252 can be attached to adaptor member 230 at one end and to a plug assembly 240 at its opposite end. Though not shown, lanyard 252 can be similarly attached to adaptor 230a. When insert probe 200 is used solely for suction and irrigation purposes and to accommodate operative instruments, insertion end 248 of plug assembly 240 is disposed within adaptor 230 of second end 234 to prevent debris and/or blood from being suctioned out through second end 234 and bypassing the suction tubing member of remote tubing assembly 20. When an operative instrument is inserted within aperture 238 of hood 235 and adaptor 234, or through adaptor 234 without hood 235, plug assembly 240 hangs loose by lanyard 252. Plug 240 may be provided with a tactile surface 250 for ease in handling.

In use, tubing members 22 and 24 are attached to luer attachments 216 and 218, as described above, and a surgical instrument is inserted through aperture 238 and adaptor 230 or just adaptor 230 depending on the size of the instrument. The operative end of the surgical instrument, when in use, extends outward of passageway 204 at end 206 of insert probe 200. When not in use, the physician merely pulls the opposite end of the surgical instrument to retract the operative end within passageway 204. To interchange surgical instruments, the physician merely pulls on the instrument to withdraw it from insert probe 200 and insert a different instrument as desired. If suction and irrigation is solely desired, plug assembly 240 is disposed within adaptor 230 at second end 234. Insert probe 200, with or without an operative instrument insert, is inserted through a trocar, such as trocar 100, to the desired operative site.

Lastly, remote tubing assembly 20 may be utilized with a handpiece 300. Hand piece 300, allows the physician to utilize surgical instruments which would normally be attached to a surgical valve without the physician concerning himself or herself with suction and irrigation functions. Hand piece 300 has a first end 302 and a second end 304, as well as a body member 306 therebetween. Body member 306 defines a passageway 308 extending from first end 302 to second end 304. A probe mount port 310 is disposed at first end 302.

Preferably, probe mount port 310 provides for a quick disconnect/connect of a surgical probe (not shown) to handpiece 300. As discussed above, co-pending invention U.S. application Ser. No. 08/286,949, shows various embodiments for the quick disconnect feature, all of which may utilized for port 310 and all of which are incorporated by reference herein. The quick disconnect mechanism allows rapid change from one probe to another.

A rear port 312 is defined at second end 304. Passageway 308 has threads 314 disposed at said rear port 312 mating with threads 318 of a plug 316. In lieu of plug 316, electrosurgical inserts and laser fiber inserts (both not shown), as well as other probes (not shown), can be inserted through passageway 308 and attached to rear port 312 by mating threads (not shown) associated with the inserts with threads 314. Furthermore, these inserts and probes may also be attached by other conventional means.

A pair of luer attachments 320 and 322 protrude outward from handpiece 300. Luer attachments 320 and 322 define internal passageways 324 and 326, respectively, which are in communication with passageway 308. Luer attachments 320 and 322 act as male insertion members for mating with female receiving luers 34 and 36 of remote tubing assembly 20 and have either mating threads or mating ramp portions 328 and 330, respectively, disposed at their distal insertion ends.

Caps 42 and 44 of luers 34 and 36, respectively, receive luer attachments 320 and 322, to connect respective tubing members 22 and 24 to handpiece 300. Once connected, passageways 23 and 25 are in communication with respective passageways 324 and 326 and, thus, in communication with passageway 308 of handpiece 200. Once the tubing members have been connected communication between valve 80 and handpiece 200 is completed thus allowing for both suction/smoke evacuation and irrigation at the operative site through handpiece 200.

Smoke and debris removed from the operative site will travel through the attached surgical probe or electro-surgical insert through passageway 308 of handpiece 300 to the associated suction/smoke evacuation luer attachment 320 or 322 and ultimately to valve 80, while irrigation will travel from valve 80 through the other luer attachment through passageway 308 and ultimately to the operative site (not shown). To connect luer attachments 320 and 322 to handpiece 300, luer attachments 320 and 322 are disposed in or threaded with corresponding apertures in the side of handpiece 300 and retained by adhesive (not shown).

In use, tubing members 22 and 24 are attached to luer attachments 320 and 322, as described above, and a surgical instrument probe is attached to probe mount port 310 or an electrosurgical insert, laser fiber insert or an other surgical probe is accommodated through rear port 312, as described above. To interchange surgical instruments, the physician merely detaches the surgical instrument attached to handpiece 300 and attaches different surgical instrument. The surgical instrument attached to handpiece 300, which has remote operation of suction/irrigation functions, is then inserted through a trocar for use at the operative site.

The present invention provides an instrument interchange reduction system providing superior advantages in endoscopic and laparoscopic instrumentation. The instrument interchange reduction system provides instantaneous suction or irrigation on demand and continuous smoke evacuation throughout the entire procedure in harmony with the operative instrument currently being used directly through the operative port. The instrument interchange reduction system extends suction/irrigation and smoke evacuation from a surgical valve to either the instrument insert probe, handpiece or one or two trocars.

Accordingly, the present invention provides instantaneous suction/irrigation on demand, continuous smoke evacuation, and the use of any 5 mm surgical instrument through one port for increased functionality to reduce instrument interchange and save time. The present invention allows for the use of shears and/or graspers with continuously available suction and irrigation to pinpoint bleeders, allowing precise cauterization to reduce clot formation, char and smoke, and enhance visualization. In addition, continuous smoke evacuation from the point of origin is achieved allowing for greater visibility and safety. Thus, the present invention provides a solution to eliminating numerous interchanges, reducing time wasted on switching instruments, and removing smoke quickly and efficiently.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A tubing assembly for supplying concurrent suction and irrigation to an operative site from a remote surgical valve of the type having an irrigation chamber, a suction chamber, and valve controls for controlling irrigation and suction flows through the chambers, said tubing assembly comprising:

a first tubing member having a first end and a second end, said first tubing member defining a first internal passageway extending from said first end to said second end;

a second tubing member having a first end and a second end, said second tubing member defining a second internal passageway extending from said first end to said second end of said second tubing member and being isolated from said first internal passageway;

a valve connection member coupled to said first ends of said first and second tubing members, said valve connection member being shaped to engage the surgical valve, said valve connection member having a first channel fluidly coupling said first passageway and one of the irrigation and suction chambers of the valve and a second channel fluidly coupling said second passageway and the other of the irrigation and suction chambers, wherein said first and second channels are isolated from each other to maintain said first and second internal passageways isolated from each other to permit concurrent irrigation through the irrigation chamber into one of said internal passageways and suction through the other of said internal passageways and the said suction chamber without interference between said first and second internal passageways; and an instrument connector coupled to said second ends of said first and second tubing members, said instrument connector being shaped to engage separate connector attachments on a surgical instrument used at the operative site and to maintain said first passageway isolated from said second passageway, such that said first and second internal passageways are isolated from each other to permit concurrent irrigation through one of said passageways and suction through the other of said passageways without interference with each other.

2. The tubing assembly of claim 1 wherein said valve connection member has a first end shaped for engaging the surgical valve and a second end shaped for engaging said first ends of said tubing members, said first and second channels of said valve connection member extending between said first and second ends of said valve connection member.

3. The tubing assembly of claim 1 wherein said valve connection member includes an isolating assembly shaped for isolating the suction chamber of the valve from the irrigation chamber of the valve.

4. The tubing assembly of claim 3 wherein said isolating assembly comprises a rod member having a first end and a second end with said first channel of said valve connection member defined therebetween, said first end of said rod member being disposed within said second channel of said valve connection member to isolate said first internal passageway from said second internal passageway and said first channel from said second channel, and to provide communication between said first internal passageway and the one of said irrigation and suction chambers of the valve.

5. The tubing assembly of claim 3 wherein said isolating assembly is a rod member having a first end and a second end with said first channel of said valve connection member defined therebetween, said second end of said rod member defining a boss member, the second end of said rod member being shaped to be disposed within the surgical valve to isolate the suction chamber of the surgical valve from the irrigation chamber of the surgical valve.

6. The tubing assembly of claim 1 wherein said instrument connector comprises at least one luer connector coupled to said second end of each of said tubing members and shaped to engage a luer attachment on a surgical instrument.

7. The tubing assembly of claim 1 further comprising a surgical handpiece coupled to said instrument connector, said instrument connector comprising a first instrument connector coupled to said second end of said first tubing member and a second instrument connector coupled to said second end of said second tubing member, said handpiece having a first tubing attachment member, a second tubing attachment member, and an internal passageway defined therein, said first tubing member being attached to said first attachment member via said first instrument connector to provide communication between said first internal passageway and the internal passageway of said handpiece, said second tubing member being attached to said second attachment member via said second instrument connector to provide communication between said second internal passageway and the passageway of said handpiece.

8. The tubing assembly of claim 1 further comprising a remote instrument insert coupled to said instrument connector, said instrument connector comprising a first instrument connector coupled to said second end of said first tubing member and a second instrument connector coupled to said second end of said second tubing member, said instrument insert having an elongated shaft for the insertion of additional surgical instruments, said elongated shaft defining a passageway therein, said instrument insert further having a first tubing attachment member and a second tubing attachment member, said second end of said first tubing member being attached to said first attachment member via said first instrument connector to provide communication between said first internal passageway and the passageway of said instrument insert, said second end of said second tubing member being attached to said second attachment member via said second instrument connector to provide communication between said second internal passageway and the passageway of said instrument insert.

9. The tubing assembly of claim 1 further comprising a trocar coupled to said instrument connector, said trocar having an internal passageway defined therein and a tubing attachment member, at least one of said tubing members being attached to said tubing attachment member to provide communication between the internal passageway of said tubing member and the passageway of said trocar.

10. The tubing assembly of claim 9 further including a y-connector member disposed between said tubing members and said tubing attachment member of said trocar, said instrument connector comprising a first instrument connector coupled to said second end of said first tubing member and a second instrument connector coupled to said second end of said second tubing member, said y-connector having a first end and a second end, said first end being attached to said tubing attachment member of said trocar, said second end of said y-connector having a second tubing attachment member and a third tubing attachment member, said first tubing member being attached to said second attachment member via said first instrument connector to provide communication between said first internal passageway and the passageway of said trocar, said second tubing member being attached to said third attachment member via said second instrument connector to provide communication between said second internal passageway and the passageway of said trocar.

11. A tubing assembly for supplying concurrent suction and irrigation to an operative site from a remote surgical valve, the surgical valve being of the type having an irrigation chamber, a suction chamber, valve controls for controlling irrigation and suction flows through each of the irrigation and suction chambers, and a common channel communicating with the irrigation chamber and suction chamber, said tubing assembly comprising:

a first tubing member having a first open end and a second open end, said first tubing member defining a first internal passageway extending from said first open end to said second open end;

a second tubing member having a first open end and a second open end, said second tubing member defining a second internal passageway extending from said first open end to said second open end of said second tubing member and isolated from said first internal passageway;

a valve attachment member coupled to said first open ends of said first and second tubing member and having a first end and a second end, said first end of said valve attachment member having a first port and a second port isolated from said first port, said first open end of said first tubing member being coupled to and in fluid communication with said first port, said first open end of said second tubing member being coupled to and in fluid communication with said second port, said second end of said valve attachment member being shaped to engage the surgical valve and to maintain said first internal passageway isolated from said second internal passageway, such that irrigation through one of said tubing members is isolated from suction through the other of said tubing members thereby permitting concurrent irrigation and suction through said isolated internal passageways of said tubing members without interference; and an instrument connector coupled to said second ends of said first and second tubing members, such that irrigation through one of said tubing members is isolated from irrigation through the other of said tubing members thereby permitting concurrent irrigation and suction through separate internal passageways of said tubing members without interference.

12. The tubing assembly of claim 11, further comprising a rod member having a first end and a second end and defining a passageway therebetween, said first end of said rod member being disposed within said valve attachment member to isolate said first port from said second port and to provide communication between said first internal passageway and the passageway of said rod member.

13. The tubing assembly of claim 12, wherein said second end of said rod member defines a boss member, the second end of said rod member being shaped to be disposed within the common channel of said surgical valve to isolate the suction chamber of the surgical valve from the irrigation chamber of the surgical valve.

14. The tubing assembly of claim 12, wherein said instrument connector has at least one luer connector coupled to said second end of each of said tubing members and shaped to engage a luer attachment of a surgical instrument.

15. The tubing assembly of claim 11, further comprising a surgical handpiece coupled to said instrument connector, said instrument connector comprising a first instrument connector coupled to said second end of said first tubing member and a second instrument connector coupled to said second end of said second tubing member, said handpiece having a first tubing attachment member and a second tubing attachment member, said handpiece defining an internal passageway therein, said first tubing member being attached to said first attachment member via said first instrument connector to provide communication between said first internal passageway and the passageway of said handpiece, said second tubing member being attached to said second attachment member via said second instrument connector to provide communication between said second internal passageway and the passageway of said handpiece.

16. The tubing assembly of claim 11, further comprising a remote instrument insert coupled to said instrument connector, said instrument connector having a first instrument connector coupled to said second end of said first tubing member and a second instrument connector coupled to said second end of said second tubing member, said instrument insert having an elongated shaft for the insertion of additional surgical instruments, said elongated shaft defining a passageway therein, said instrument insert also having a first tubing attachment member and a second tubing attachment member, said first tubing member being attached to said first attachment member via said first instrument connector to provide communication between said first internal passageway and the passageway of said instrument insert, said second tubing member being attached to said second attachment member via said second instrument connector to provide communication between said second internal passageway and the passageway of said instrument insert.

17. The tubing assembly of claim 11, further comprising a trocar coupled to said instrument connector, said trocar having a tubing attachment member, said trocar defining an internal passageway therein, at least one of said tubing members being attached to said tubing attachment member via said instrument connector to provide communication between the internal passageway of said tubing member and the passageway of said trocar.

18. The tubing assembly of claim 17 further including a y-connector member disposed between said instrument connector on said tubing members and said tubing attachment member of said trocar, said instrument connector comprising a first instrument connector coupled to said second end of said first tubing member and a second instrument connector coupled to said second end of said second tubing member, said y-connector having a first end and a second end, said first end being attached to said tubing attachment member of said trocar, said second end of said y-connector having a second tubing attachment member and a third tubing attachment member, said first tubing member being attached to said second tubing attachment member via said first instrument connector to provide communication between said first internal passageway and the passageway of said trocar, said second tubing member being attached to said third tubing attachment member via said second instrument connector to provide communication between said second internal passageway and the passageway of said trocar.

19. A tubing assembly for supplying concurrent suction and irrigation to an operative site from a remote surgical valve, the surgical valve having an irrigation chamber, a suction chamber, and a common channel communicating with the irrigation chamber and suction chamber, said tubing assembly comprising:

a first tubing member having a first end and a second end, said first tubing member defining a first internal passageway extending from said first end to said second end;

a second tubing member having a first end and a second end, said second tubing member defining a second internal passageway extending from said first end to said second end of said second tubing member;

a valve attachment member having a first end and a second end, said first end defining a first internal port and a second internal port, the first end of said first tubing member disposed within said first internal port and the first end of said second tubing member disposed within said second internal port, the second end of said valve attachment member being shaped for removable connection to the surgical valve;

a rod member having a first end and a second end and defining a passageway therebetween, said second end of said rod defining a boss member, the second end of said rod being shaped to be disposed within a surgical valve to isolate the suction chamber from the irrigation chamber, said first end of said rod being disposed within said attachment member to isolate said first internal port from said second internal port to isolate said first passageway from said second passageway, and to provide communication between said first internal passageway and the passageway of said rod;

a first luer member disposed at the second end of such first tubing member; and a second luer member disposed at the second end of said second tubing member, at least one of said first luer and said second luer being shaped for removable connection to a surgical instrument used at the operative site.

20. The tubing assembly of claim 19, further including a handpiece coupled to said first and second luer members, said handpiece having a first luer attachment member and a second luer attachment member, said handpiece defining an internal passageway therein, said first luer member being attached to said first luer attachment member to provide communication between said first internal passageway and the passageway of said handpiece, said second luer member being attached to said second luer attachment member to provide communication between said second internal passageway and the passageway of said handpiece.

21. The tubing assembly of claim 19, further comprising a remote instrument insert coupled to said first and second luer members, said instrument insert having an elongated shaft for the insertion of additional surgical instruments, said elongated shaft defining a passageway therein, said instrument insert having a first luer attachment member and a second luer attachment member, said first luer member being attached to said first luer attachment member to provide communication between said first internal passageway and the passageway of said instrument insert, said second luer member being attached to said second luer attachment member to provide communication between said second internal passageway and the passageway of said instrument insert.

22. The tubing assembly of claim 19, further comprising a trocar coupled to said first and second luer members, said trocar having a luer attachment member, said trocar defining an internal passageway therein, at least one of said luer members being attached to said luer attachment member to provide communication between the internal passageway of the associated tubing member and the passageway of said trocar.

23. The tubing assembly of claim 22 further including a y-connector member disposed between said luer members and said luer attachment member of said trocar, said y-connector having a first end and a second end, said first end being attached to said luer attachment member of said trocar, said second end of said y-connector having a second luer attachment member and a third luer attachment member, said first luer member being attached to said second luer attachment member to provide communication between said first internal passageway and the passageway of said trocar, said second luer member being attached to said third luer attachment member to provide communication between said second internal passageway and the passageway of said trocar.

* * * * *